United States Patent [19]

Morton, Jr.

[11] 4,094,891

[45] June 13, 1978

[54] CIS-13-9-DEOXY-9,10-DIDEHYDRO-PGD$_2$ COMPOUNDS

[75] Inventor: Douglas Ross Morton, Jr., Portage, Mich.

[73] Assignee: The Upjohn Company, Kalamazoo, Mich.

[21] Appl. No.: 755,990

[22] Filed: Dec. 30, 1976

Related U.S. Application Data

[62] Division of Ser. No. 614,242, Sept. 17, 1975, Pat. No. 4,016,184.

[51] Int. Cl.$^2$ .......................................... C07C 121/00
[52] U.S. Cl. ................................. 260/413; 260/408; 260/410; 260/410.5; 260/410.9 R; 260/514 D; 560/121
[58] Field of Search ............ 260/468 D, 514 D, 408, 260/410, 410.9 R, 410.5, 413

[56] References Cited

U.S. PATENT DOCUMENTS

3,954,844   5/1976   Colton et al. ........................ 260/488

*Primary Examiner*—Robert Gerstl
*Attorney, Agent, or Firm*—Robert A. Armitage

[57] ABSTRACT

Prostaglandin analogs with the following cyclopentane ring structure:

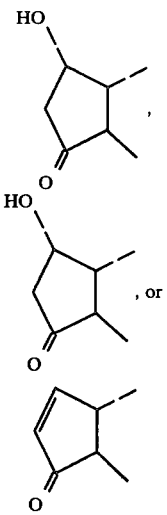

are disclosed along with intermediates useful in their preparation and processes for their preparation. These analogs are useful for the same pharmacological purposes as the prostaglandins, particularly and especially as blood platelet aggregation inhibitors.

9 Claims, No Drawings

CIS-13-9-DEOXY-9,10-DIDEHYDRO-PGD$_2$ COMPOUNDS

The present application is a divisional application of Ser. No. 614,242, filed Sept. 17, 1975, now issued as U.S. Pat. No. 4,016,184, on Apr. 5, 1977.

The present invention relates to prostaglandin analogs for which the essential material constituting a disclosure therefor is incorporated by reference here from U.S. Pat. No. 4,016,184, issued Apr. 5, 1977.

I claim:

1. A prostaglandin analog of the formula

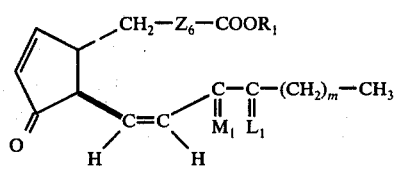

wherein $m$ is one to 5, inclusive; wherein $M_1$ is

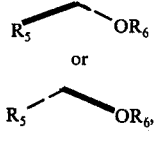

or

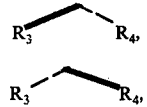

wherein $R_5$ and $R_6$ are hydrogen or methyl, with the proviso that one of $R_5$ and $R_6$ is methyl only when the outer is hydrogen; wherein $L_1$ is

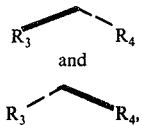

or a mixture of

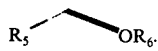

and

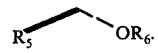

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; and wherein $Z_6$ is (1) cis—CH=CH—CH$_2$—(CH$_2$)$_g$—CF$_2$—, (2) cis—CH=CH—CH$_2$—(CH$_2$)$_g$—CH$_2$—, or (3) cis—CH$_2$—CH=CH—(CH$_2$)$_g$—CH$_2$—, wherein g is one, 2, or 3.

2. A compound according to claim 1, wherein $M_1$ is

3. A compound according to claim 1, wherein $M_1$ is

4. A compound according to claim 3, wherein m is 3.

5. A compound according to claim 4, wherein g is 3.

6. 2a,2b-Dihomo-9-deoxy-9,10-didehydro-15-epi-cis-13-PGD$_2$, a compound according to claim 5.

7. A compound according to claim 4, wherein g is one.

8. 9-Deoxy-9,10-didehydro-15-epi-cis-13-PGD$_2$, a compound according to claim 7.

9. cis-4,5-Didehydro-9-deoxy-9,10-didehydro-15-epi-cis-13-PGD$_1$, a compound according to claim 7.

* * * * *

UNITED STATES PATENT OFFICE
CERTIFICATE OF CORRECTION

Patent No. 4,094,891     Dated June 13, 1978

Inventor(s) Douglas Ross Morton, Jr.

It is certified that error appears in the above-identified patent and that said Letters Patent are hereby corrected as shown below:

Before the claims, please add:

-- In addition to the various examples described above, the present invention further comprises the preparation and use by the above-described methods of the following additional compounds:
  2a,2b-Dihomo-9-deoxy-9,10-didehydro-15-epi-cis-13-$PGD_2$;
  9-deoxy-9,10-didehydro-15-epi-cis-13-$PGD_2$; and
  cis-4,5-Didehydro-9-deoxy-9,10-didehydro-15-epi-cis-13-$PGD_1$. --

Signed and Sealed this

Sixteenth Day of January 1979

[SEAL]

Attest:

RUTH C. MASON
Attesting Officer

DONALD W. BANNER
Commissioner of Patents and Trademarks